United States Patent [19]

Gray et al.

[11] Patent Number: 5,232,625
[45] Date of Patent: Aug. 3, 1993

[54] CYANO-ALICYCLIC ESTERS IN LIQUID CRYSTAL COMPOSITIONS

[75] Inventors: George W. Gray; Kenneth J. Toyne; David Lacey, all of North Humberside; David Holmes, Durham; Richard M. Scrowston, North Humberside, all of England

[73] Assignee: The Secretary of State for Defence in her Britannic Majesty's Government of the United Kingdom of Great Britain and Northern Ireland, United Kingdom

[21] Appl. No.: 877,138

[22] Filed: May 1, 1992

Related U.S. Application Data

[62] Division of Ser. No. 359,790, Jun. 1, 1989, Pat. No. 5,147,577.

[30] Foreign Application Priority Data

Dec. 8, 1987 [GB] United Kingdom ............... 8629322

[51] Int. Cl.$^5$ .................. C09K 19/30; C09K 19/12; C09K 19/20; C07C 255/00
[52] U.S. Cl. .................. 252/299.63; 252/299.66; 252/299.67; 359/104; 558/426
[58] Field of Search ............ 252/299.1, 299.63, 299.65, 252/299.66, 299.67; 359/104; 558/426

[56] References Cited

U.S. PATENT DOCUMENTS

| | | | |
|---|---|---|---|
| 4,600,528 | 7/1986 | Eidenschink et al. | 252/299.61 |
| 4,659,499 | 4/1987 | Ferrato | 252/299.1 |
| 4,693,841 | 9/1987 | Hittich et al. | 252/299.62 |
| 4,707,295 | 11/1987 | Pohl et al. | 252/299.62 |
| 4,713,196 | 12/1987 | Praefche et al. | 252/299.01 |
| 4,784,793 | 11/1988 | Coates et al. | 252/299.62 |
| 4,830,470 | 5/1989 | Buchecker et al. | 252/299.01 |
| 4,886,620 | 12/1989 | Hopt et al. | 252/299.61 |
| 5,002,694 | 3/1991 | Wachtler et al. | 252/299.61 |
| 5,180,521 | 1/1993 | Eidenschink et al. | 252/299.61 |

FOREIGN PATENT DOCUMENTS

61-10544  1/1986  Japan .

Primary Examiner—Robert L. Stoll
Assistant Examiner—Shean C. Wu
Attorney, Agent, or Firm—Nixon & Vanderhye

[57] ABSTRACT

Compounds suitable for use as constituents of ferroelectric smectic liquid crystal compositions, which are esters of formula (I), where $R_2$ and $R_3$ together represent the residue of an alicyclic hydrocarbon ring system where °C. is an asymmetric carbon atom and X is a chain of up to three linked aromatic or alicyclic six-membered organic cyclic groups, laterally and/or terminally substituted. Preferred compounds have a formula (II), where $R_1$ is alkyl or alkoxy, A, B, and D are phenyl, fluoro or chloro substituted phenyl or cyclohexyl, n is 0 or 1, Y is a bond or $CH_2CH_2$ if n is 0, or a bond $CH_2CH_2COO$ or COO if n is 1. Preferred groups $C(CN)R_2R_3$ are formula (III) and (IV).

10 Claims, 2 Drawing Sheets

Fig.2.

CYANO-ALICYCLIC ESTERS IN LIQUID CRYSTAL COMPOSITIONS

This is a division of application Ser. No. 07/359,790, filed Jun. 1, 1989 now U.S. Pat. No. 5,147,577.

This invention relates to novel cyano-alicyclic esters and to liquid crystal materials containing them. In particular the invention relates to chiral derivatives and ferroelectric smectic liquid crystal compositions containing them.

Ferroelectric smectic liquid crystal materials are known, (e.g. N. A. Clark et al: Appl Phys Lett (1980) 36 899), and exploit the electro-optical properties of the ferroelectric chiral smectic phase. The chiral smectic C (abbreviated $S_C^*$ the asterisk denoting chiralty) is most used as it is the most fluid, but other chiral smectic phases e.g. I, F, J, K, G, H or X may also be used.

Although some ferroelectric smectic liquid crystal materials are single compounds it is more usual for such a material to be a composition. Generally such a composition contains one or more compounds which either singly or together show an $S_C$ phase (termed a smectic "host"), together with one or more chiral (i.e. optically active) compounds which are generally added to induce the smectic material to show a high spontaneous polarisation. Ps. The composition may also contain additives. For example to broaden the $S_C^*$ range, to suppress undesirable phases, or optically active compounds to modify the helical pitch of the $S_C^*$ phase.

Among the features sought in a good ferroelectric smectic liquid crystal material are low viscosity, fast switching speeds, a broad $S_C^*$ phase range, and a high spontaneous polarisation coefficient Ps and a long helical pitch. In view of the high cost of synthesis of optically pure compounds it is also desirable that the chiral compound is cheap.

Optically active compounds used in ferroelectric smectic liquid crystal compositions generally consist of a "core" consisting of a chain of linked cyclic groups, with an optically active group containing an asymmetric carbon atom at or near a terminal position of the chain. The core is selected from the reasonably well known combinations of cyclic groups which encourage the compound to be miscible with smectic liquid crystal phases. The goal of much research in ferroelectric smectic liquid crystal chemistry is to identify novel optically active groups which may be combined with such cores to form advantageous compounds.

Many suitable optically active compounds are known. In WO86/04328 also Mol. Cryst. Liq. Cryst., Serie II, 3(6), (1986) p189–195, compounds are described wh ch are derivatives of chiral terpenoid alcohols, such as being a menthol derivative. These compounds generally induce a relatively low Ps in smectic mixtures.

PCT/GB 87/00441 and JPA-61-243055 describe compounds of structure where R is alkyl. These compounds show a high Ps. Both have publication dates later than the priority date of this application.

JP-A-6110544 describes liquid crystal compounds which contain a group where R is alkyl, combined with a mesogenic core, C. R. Acad. Sc. Paris, t 272 (May 27, 1971) describes compounds of formula where the $CH_3$ group is in the 4- or 3-position relative to the COO— link.

It is an object of the present invention to provide novel compounds which are suitable optically active constituents of ferroelectric liquid crystal compositions, and which have advantageous properties relative to known compounds.

According to the invention there is provided a compound, suitable for use as a constituent of a ferroelectric smectic liquid crystal composition, which is an ester of formula I:

wherein $R_2$ and $R_3$ together represent the residue of an alicyclic hydrocarbon ring system in which C* is an asymmetrically substituted carbon atom, and X is a core consisting of a chain of up to three independently selected aromatic or aliphatic six-membered organic cyclic groups, which may be laterally and/or terminally substituted, and linked by single bonds or via linking groups, provided that if the group $C^*.CN.R_2R_3$ is where $R_4$ indicates that the cyclohexane ring system carries one or more $C_1$ to $C_6$ alkyl substituents $R_4$ the substitution pattern of which is such that the position indicated * is asymmetrically substituted, then X is a group of general formula:

where $R_1$ represents $C_1$–$C_{12}$ alkyl or alkoxy, rings A, B and D independently represents phenyl, fluoro or chloro substituted phenyl, or cyclohexyl, n is 0 or 1, Y may be a single bond or $CH_2CH_2$ if n is 0, or may be a single bond, $CH_2CH_2COO$ or COO if n is 1.

The inventors have discovered that compounds which contain the alicyclic hydrocarbon ring system of Formula I combined with a suitable core X may be extremely useful constituents of ferroelectric smectic liquid crystal compositions. The structural preferences discussed below are chosen inter alia with regard to suitability for use in such liquid crystal compositions. For example from the point of view of identifying compounds which appear to have a high spontaneous polarisation or are easy to prepare.

It is preferred therefore that the alicyclic hydrocarbon ring system in formula I is a terpenoid ring system, which may be selected from any terpenoid ring system which has a substitution pattern that allows the atom C* to be asymmetrically substituted. The ring system may be monocyclic, bicyclic or tricyclic.

Terpenoids are derivatives of the analogous terpenes, which are isoprene oligomers. The term 'terpenoid' as used herein includes not only the saturated or unsaturated isoprene oligomers themselves but also their oxygenated derivatives and partial or complete reduction products. The majority of terpenoids contain cyclic polyisoprene chains. Preferred chains are those based on six-membered rings, substituted and/or bridged. Terpenoids are obtained from biosynthetic sources and in the course of biosynthesis terpenes are sometimes produced which either lack part of an isoprene unit or have part of an extra one. Sometimes migration of methyl groups occurs during biosynthesis so that the final biosynthetic product may no longer have a skeleton strictly composed of isoprene units. These compounds are nevertheless considered to be members of the terpenoid family.

Such a ring system may exist in a number of isomeric forms depending upon the conformation of the cyclic system, and in addition to other effects this may confer either (+) or (−) senses of optical activity or R or S absolute configurations on the asymmetric centre C*. All such isomeric forms are included in the invention. Some examples of cyclic terpenoid groups of formula encompassed by formula I are the terpenoid-based ring systems listed below in table 1. Conventional line formulae are used.

TABLE 1

| | |
|---|---|
|  | 1.1 |
|  | 1.2 |
|  | 1.3 |
|  | 1.4 |
|  | 1.5 |
|  | 1.6 |
|  | 1.7 |
|  | 1.8 |

TABLE 1-continued 1.9

Structure 1.1 is particularly preferred.

The structures listed in table 1 are all derived from naturally occurring terpendoid systems, for example 1.1 is derived from the ring system found in camphor (1,7,7-trimethylbicyclo(2,2,1)-2-heptanone). As biosynthesis often yields isomeric compounds in single optically pure isomeric forms, this means that such cyclic systems may be derived via natural products without the expensive and tedious necessity of stereospecific synthesis or optical resolution.

Another type of alicyclic hydrocarbon ring system which may be represented by:

in formula I is:

where ($R_4$) indicates that the cyclohexane ring system carries one or more (preferably one) $C_1$-$C_6$ alkyl group (preferably methyl) substituents, which may be the same or different, the substitution pattern being such that the position indicated by * is asymmetrically substituted.

A large range of combinations of cyclic groups and links between these are suitable as the core X which may be combined with the asymmetrically substituted alicyclic hydrocarbon ring system in a compound of Formula I. Many such would be well known to those skilled in the liquid crystal art, having been proposed for use with other groups containing asymmetric carbon atoms. For example suitable cores are described in EPA 115693 (combined with optically active alkoxy), EPA 136845 (combined with optically active —COO-alkyl, alkoxy, or alkyl), EPA 152217 (combined with optically active OCOO-alkyl), EPA 153826 (combined with optically active alkoxy), EPA 159872 (combined with optically active OOC—CH(X)-alkyl where X is halogen), EPA 160416 (combined with optically active alkoxy), EPA 164814 (combined with optically active alkyl or alkoxy), EPA 167328 (combined with optically active alkoxy or alkylcarbonyloxy), EPA 168963 (combined with optically active alkylcarbonyloxy), EPA 174191 (combined with optically active —Z-alkyl where Z is a single bond, O, CO, OOC or OCOO), EPA 188222 (combined with optically active COO-alkyl), EPA 191600 (combined with optically active —Y—CH(T)-alkyl or haloalkyl), EPA 192267 (combined with optically active (CO)—O-alkyl), and PCT/JP85/00302.

The numerous examples of known cores mentioned above demonstrate the range of structures which may be combined with the alicyclic hydrocarbon ring system contained in the compound of formula I to provide a useful component of a ferroelectric liquid crystal composition.

A number of cores X have been identified to be particularly suitable to be used in the compound of formula I, based upon the criteria of preference referred to above. Preferred compounds of formula I containing these cores are therefore defined by formula IA below:

IA where $R_1$ represents $C_1$-$C_{12}$ alkyl or alkoxy, rings A, B and D independently represents phenyl, fluoro or chloro substituted phenyl, or cyclohexyl, n is 0 or 1, Y may be a single bond or $CH_2 CH_2$ if n is 0, or may be a single bond, $CH_2 CH_2COO$ or COO if n is 1.

$R_2$ and $R_3$ are as defined with respect to formula I above. Preferably $R_1$ is $C_3$-$C_{10}$ n-alkyl or n-alkoxy, especially n-octyloxy. Examples of particularly preferred cores in compounds of formula IA are listed in table 2 below:

TABLE 2

2.1

2.2

2.3

2.4

2.5

2.6

TABLE 2-continued

Of these, structures 2.1, 2.3 and 2.4 are especially preferred. (F) indicates that one or more fluorine substituents may be present on the ring, preferably one.

Compounds of formula I and IA may be prepared by relatively straightforward esterification routes such as:

which may be carried out using fairly standard esterification reagents and conditions between an appropriate acid (i) and the cyanohydrin (ii).

When the alicyclic hydrocarbon ring system is derived from a terpenoid, the terpenoid cyanohydrin if not commercially available, may be prepared from a suitable terpenoid ketone, many of which are commercially available. If necessary the terpenoid ketone may itself be prepared from a commercially available terpenoid precursor such as from a terpenoid secondary alcohol by oxidation.

Examples of suitable terpenoid ketones, and the terpenoid ring systems listed in table 1 which may be prepared from them include: Camphors (1.1), the methones (1.2), carvones (1.3), fenchones (1.5), and verbenones (1.8).

Examples of suitable terpenoid alcohols which may be oxidised e.g. by Cr (VI) to terpenoid ketones, and the corresponding terpenoid ring systems listed in table 1 which may be prepared from them include: borneols (1.1), menthols (1.2), isopinocampheols (1.6), isopulegols (1.7) and verbenols (1.3 and 1.9).

Using known methods, unsaturated sites on such structures as 1.3 or 1.7 or 1.8 listed in table 1 may be modified by addition or reduction to produce modified terpenoid systems, e.g. structures 1.4 and 1.9 may be produced from structures 1.3 and 1.8 respectively by reduction. This can be used to modify the conformation of the cyclic system.

As they can be made from naturally occurring optically pure terpenoid compounds such as alcohols and ketones, which are often very cheap relative to wholly synthetic optically pure compounds, compounds of formula I have a significant price advantage over synthetic alternatives.

Figure 1:
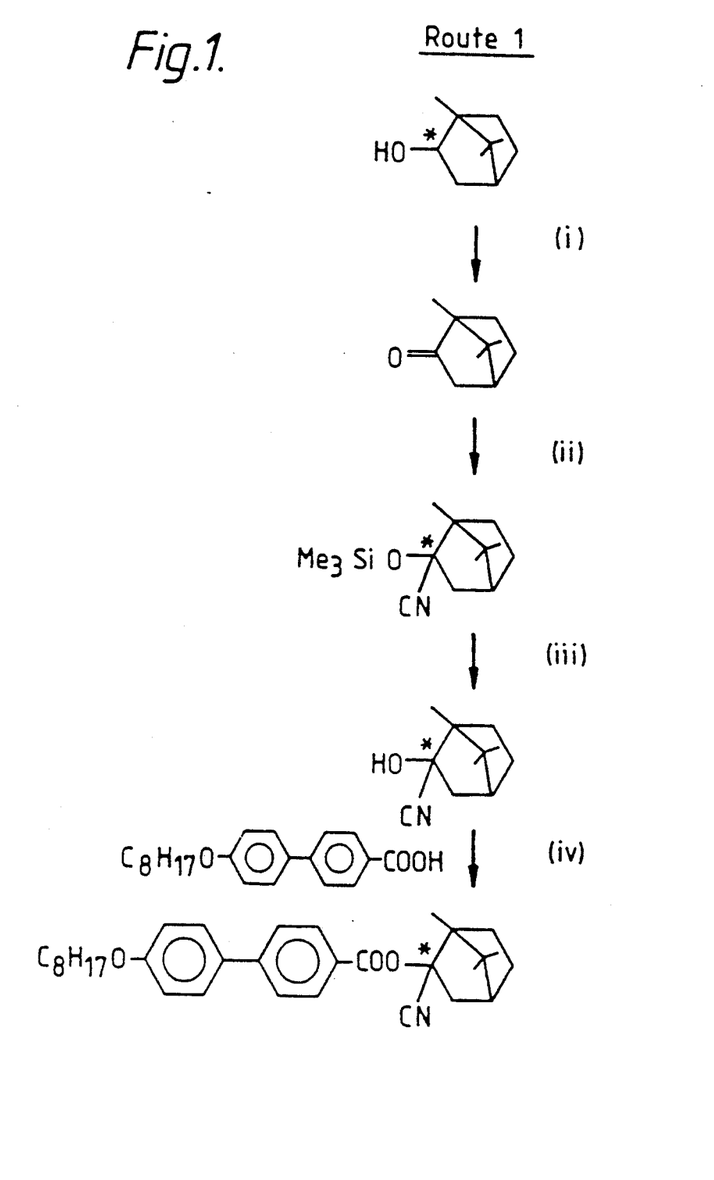
FIG. 1 Which shows a preparative route for compounds of Formula I.

Starting from a terpenoid alcohol, the terpenoid cyanohydrin may be prepared for example by steps (i) to (iii) of route 1 shown in FIG. 1. Other routes will be apparent to those skilled in the field.

When the compound of formula I contains the group:

as defined above, a suitable cyanohydrin may be prepared from the corresponding cyclohexanone by reaction with hydrogen cyanide, i.e.:

Many such cylohexanones are known e.g. 3-methyl-cyclohexanone.

When the cyanohydrin is prepared in these ways it may be formed as a mixture of the optical isomers which will need to be resolved if optically pure compounds are required. Known methods may be used for this. Route 1 is generally stereo-specific.

Many carboxylic acids are commercially available which contain suitable cores X. When not available they may be synthesised from simple precursors, and acquisition of a suitable acid will therefore present no problem to one skilled in the art.

According to a further aspect of the invention there is provided a ferroelectric smectic liquid crystal material, being a mixture of compounds, at least one of which is a compound of formula I. In this mixture the compound of formula I is preferably in an optically active isomeric form.

Compounds of formula I may be mixed with a wide range of smectic hosts to form a useful ferroelectric smectic liquid crystal composition. Such compositions containing them frequently have high Ps values, often combined with a long helical pitch in the Sc* phase.

Although this invention is not limited by any particular theory, it is possible that the advantageously high Ps in such mixtures may be due to the "locking" of the dipole of the CN group into the quite rigid asymmetrically substituted environment of the alicyclic hydrocarbon ring system.

Preferred hosts include:

The compounds described in PCT/GB86/0040, e.g. of formula II where Ra and Rb are independently $C_3-C_{12}$ alkyl or alkoxy.

The fluoro-terphenyls described in EPA 8430494.3 and GBA 8725928, i.e. of formula III where Ra and Rb are independently $C_3$-$C_{12}$ alkyl or alkoxy.

The cyano cyclohexyls of formula IV where Ra and Rb are independently $C_3$-$C_{12}$ alkyl or alkoxy.

Mixtures containing mixed fluoroterphenyls and cyanocyclohexyls (i.e. III plus IV) are especially preferred as they can be electrically switched very quickly.

The mixture may also contain additives, es to broaden the temperature range over which the Sc* phase persists, e.g. of formula V where Ra and Rb are independently $C_1$-$C_{12}$ alkyl or alkoxy.

Although ferroelectric smectic mixtures containing a compound of formula I often show quite large helical pitches, it may be advantageous to include in the mixture at least two optically active compounds, at least one being a compound of formula I, which induce the formation of Sc* phases of opposite helical pitch sense. By varying the relative proportions of these the pitch length may be adjusted. At least two of these compounds may for example be compounds of formula I. Other optically active compounds which may be used in this way include:

The amides disclosed in PTC/GB87/00223, for example VI

The terphenyls disclosed in GBA8703103, which are particularly suitable when the mixture contains terphenyls of formula III, e.g. VII:

where Ra and Rn in formulae VI and VII are independently $C_1$-$C_{12}$ n-alkyl or n-alkoxy.

The mixture according to this aspect of the invention may also contain racemic mixtures of compounds of formula I, and may typically have the following composition, expressed in weight percent.

| Host compound(s) | 30-99% |
|---|---|
| Optically active compound(s) of formula I | 5-50% |
| Other optically active compounds | 0-20% |
| Additives | 0-20% |
| Racemic compound(s) of formula I | 0-50% |

The total being 100 weight %. The nature and relative proportions of the various components of a mixture of the invention will depend upon the use for which it is intended and some experimentation may be necessary, along lines which are well known to those skilled in the art.

According to a further aspect of this invention there is provided a liquid crystal electro-optical display device which uses a ferroelectric smectic liquid crystal material which is a mixture of compounds at least one of which is a compound of formula I.

The liquid crystal materials of the invention may be used in any of the known types of ferroelectric smectic liquid crystal display device, e.g. the "Clark-Lagerwall Device" described in Appl. Phys Lett (1980), 36 899 and in Recent Developments in Condensed Matter Physics (1981), 4,309. The physics of this type of device and the method of constructing it are well known, and are described for example in PCT/GB85/00512, and PCT/GB86/0040. In practice such a device usually consists of two substrates, at least one of which is optically transparent, electrodes on the inner surfaces of the substrates by which a voltage may be applied and a layer of the liquid crystal material sandwiched between the substrates. The materials of the invention may be used in both the birefringence type display mode and the guest-host type display mode of the Clark-Lagerwall device. The device may for example be in the form of a clock, calculator or video screen display, and methods of making the device in this form will be well known to those skilled in the art.

The invention will now be described by way of example only with reference to.

EXAMPLE 1

Preparation of:

(a compound having a terpenoid ring of structure 1.1 above) The route shown in FIG. 1 was used. As the starting terpenoid was a ketone, camphor, step 1(i) was not used.

Step 1(ii)

(+)-Camphor (1.52 g 0.01 mol), trimethylsilyl cyanide (1.1 g, 0.001 mol) and zinc iodide (30 mg) were refluxed in dichloromethane (40 ml) for 24 hours. The solvent was removed by evaporation and the residue purified by distillation under reduced pressure, affording the required 0-trimethyl silylcyanohydrin (II) as an oil. 1.95 g (77% yield) was obtained, bp 70° C./0-01 mm Hg.

(II)

Step 1(iii)

Compound (II) (5.02 g, 0.02 mol) was dissolved in a mixture of tetrahydrofuran (80 ml) and 5M hydrochloric acid (10 ml) and allowed to stand at room temperature for 10 days. The mixture was diluted with water (IL) and extracted into dichloromethane (3×). The combined dichloromethane extracts were dried (MgSO4) The dichloromethane was evaporated and the solid product was recrystallised from light petroleum (Bp<40° C.), with cooling in liquid nitrogen, to give the camphor cyanohydrin (III) as a white solid. 2.3 g (65%) was obtained mp 193° C. (decomposed), $[\alpha]_{25}^D = 3.7°$ (III)

Step 1(iv)

4¹-Octyloxybiphenyl-4-carboxylic acid (1.63 g 0.005 mol), camphor cyanohydrin (III) (0.99 g, 0.0055 mol), DCC (1.13 g, 0.0055 mol) and 4-PPY (75 mg) were stirred in dichloromethane (75 ml) for 3 days. The precipitate was removed by filtration and the filtrate was washed successively with 5% aqueous acetic acid, water and saturated aqueous sodium bicarbonate solution. After drying (MgSO4) the solvent was removed by distillation under reduced pressure and the residue was subjected to column chromatography, eluting with dichloromethane. Recrystallisation from light petroleum (bp 40°-60° C.) gave the ester (I) as a white solid. 0.45 g (18%) was obtained, mp 98°-9° C.; $[\alpha]_{25}^D = -22.7°$.

The properties of a ferroelectric smectic liquid crystal material which consisted of 10 weight % of compound (I) dissolved in a smectic mixture (called hereafter 'H1') of composition:

1:1:1 by weight were measured:

Extrapolated $P_S$ at 10° C. below $T(S_C-S_A) = 78$ nCcm$^{-2}$
Extrapolated $P_S$ at 30° C. below $T(S_C-S_A) = 128$ nCcm$^{-2}$
Tilt angle of $S_C*$ phase = 13° (coloured extinction)
Sense of polarisation = (+)
Sense of N* = (D)
Extrapolated nematic (N*) pitch (measured in E7 at room temperature) } 1.12μ (laser diffraction) 1.36μ (Carnot wedge)
E7 is a nematic liquid crystal material of composition:

51 wt. %

25 wt. %

16 wt. %

8 wt. %

The formation of a long pitch N* phase when mixed with a nematic liquid crystal material is a good indication of formation of a long pitch $S_C*$ phase in a ferroelectric liquid crystal material.

The ferroelectric smectic liquid crystal material formed in this example could be used in a Clark-Lagerwall device.

EXAMPLE 2

The carboxylic acid:

was prepared using the method described in GBA 861509S. This acid was esterified with the cyanohydrin prepared in example 1 to yield the compound:

which showed a solid crystal to isotropic liquid transition at 68°-70° C.

EXAMPLE 3

The carboxylic acid referred to in example 2 was esterified with 4-hydroxybenzoic acid to yield the further acid which was esterified with the cyanohydrin of example 1 to yield:

which showed the liquid crystal transitions (°):

S₇93S_B135S_C147.1S_A177.9I

The compound prepared in this example shows a smectic C phase which demonstrates its miscibility with Sc liquid crystal materials.

EXAMPLE 4

Preparation of

3'-fluoro-4'-octoxybiphenyl-4-carboxylic acid was first prepared by the following method:

4-Bromo-2-fluorooctoxybenzene (95 g) (made by standard bromination of 2-fluorooctoxybenzene) was dissolved in dry tetrahydrofuran (250 ml) and slowly added to a mixture of magnexium turnings (8.5 g) and tetrahydrofuran (50 ml) containing a crystal of iodine. The Gagnard reaction was initiated by heating the solution. After the addition of bromide solution the mixture was stirred and refluxed under nitrogen for one hour. This solution was then transferred via a flexi-needle into a solution of triisopropylborate (123 g) in tetrahydrofuran (10 ml) at −70° C. in a nitrogen atmosphere over 30 minutes. The mixture was then allowed to warm up to room temperature over 3 hrs. 10% HCL was added to the mixture and the organic layer separated, washed with brine, dried and solvent removed. The crude solid was dried in vacuc at 20° C. Yield 80.4 g.

The product (32.2 g) in methylated spirits (50 ml) was added to a mixture of palladium tetra (triphenylphosphine) (0.6 g), tolvene (200 ml), methyl 4-bromobenzoate (21.5 g) and a 2M solution of sodium carbonate (100 ml). The mixture was heated under reflux and stirred vigorously for 16 hrs. After cooling, the reaction mixture was poured into water and the organic layer separated. The aqueous layer was extracted twice with toluene and the combined organic layers washed once with water. The solvent was removed, and the dark brown solid chromatographed on alumina (100 g) using a mixture of dichloromethane and petroleum ether. Yield 46.9 g. After crystallisation from methylated spirits the yield was 24.4 g: mp 90° C. HPLC 99.9%.

The product (19.5 g) was stirred and heated under reflux for 2 hours with potassium hydroxide (8.4 g), water (30 ml) and methylated spirits (100 ml). The solution was poured into water (100 mls) and acidified with conc. HCL. The solid was filtered off, washed with water and dried in vacuo. The crude product was purified by crystallisation from acetic acid to a purity by HPLC of 99.6%.

This acid was esterified with the cyanohydrin of example 1 to yield the optically active product, using the esterification conditions of example 1.

EXAMPLE 5

By methods analogous to those of examples 1 to 4 above, using an appropriate known acid, the following compounds were also prepared:

EXAMPLE 6

A ferroelectric smectic liquid crystal mixture was prepared having a composition:

} 95 wt %

— 5 wt %

This mixture had the following properties:
(1) Liquid crystal transitions: room temperature and below Sc*
   Sc* to N transition 62° C.
   N to I transition 120° C.
(2) Electro-optic switching:
   at 30° C. a response time of 175 μsec, using 50 V pulse and 6 V ac to latch.
(3) Ferroelectric properties:

| Temp. (°C.) | Tilt (°) | Ps (nC/cm²) |
|---|---|---|
| 650 | 11 | |
| 59 | | 1.96 |
| 55 | 17.5 | 2.85 |
| 50 | 20 | 3.53 |
| 40 | 23. | 4.89 |
| 30 | 26.5 | 6.42 |
| 25 | 26.5 | 6.99 |

EXAMPLE 7

A ferroelectric smectic liquid crystal mixture was prepared having a composition (in weight %):

| Structure | wt % |
|---|---|
| 6.0—[Ph]—[Ph(F)]—[Ph]—5 | 8.25 |
| 4.0—[Ph]—[Ph(F)]—[Ph]—5 | 12.2 |
| 8.0—[Ph]—[Ph(F)]—[Ph]—5 | 11.05 |
| 10—[Ph]—[Ph(F)]—[Ph]—5 | 6 |
| 8—[Ph]—[Ph]—[Cy]—C(4)(CN) | 18.75 |
| 8.0—[Ph]—[Ph]—[Cy]—C(8)(CN) | 18.75 |
| 8.0—[Ph]—[Ph]—COO—[Ph(F)]—5 | 20 |
| 8.0—[Ph]—[Ph]—COO—*[bornyl/CN] | 5 |

Note: in the formulae above 6.0 represents $C_6H_{13}O-$, 8 represents $C_8H_{17}-$ etc The mixture had the properties: room temperature and below $S_C^*$, $S_C^*-S_A$ 70.2° C., $S_A-N^*$ 71° C., $N^*-I$ 115° C. electro-optic switching time: response time 100 μsec at 30° C. using a 50 V pulse and 16 V ac to latch the mixture.

| Temp. (°C.) | Tilt (°) | Ps (nCcm$^{-2}$) |
|---|---|---|
| 70 | 2 | |
| 65 | 14 | 3.22 |
| 60 | 16.5 | 4.0 |
| 50 | 20 | 5.13 |
| 40 | 21.5 | 6.51 |
| 30 | 25 | 8.63 |
| 25 | 23.5 | 8.59 |

No transitions were observed under the microscope between 25°–40° C. Differential scanning calorimetry showed no peaks between 0°–40° C.

EXAMPLE 8

A ferroelectric smectic liquid crystal mixture was prepared having a composition:

| Structure | wt % |
|---|---|
| $C_8H_{17}$—[Ph]—[Ph]—[Cy](C$_4$H$_9$)(CN) | 38 wt % |
| $C_8H_{17}O$—[Ph]—[Ph]—[Cy](C$_8$H$_{17}$)(CN) | 38 wt % |
| $C_8H_{17}O$—[Ph]—COO—[Ph(F)]—$C_5H_{11}$ | 19 wt % |
| $C_8H_{17}O$—[Ph]—[Ph]—CH$_2$CH$_2$—COO—*[bornyl/CN] | 5 wt % |

This mixture showed liquid crystal transitions (°C.): room temperature and below $S_C^*$, $S_C^*-S_A$ 62.5, $S_A-N$ 73, N-I 101.4

At 30° C. response time to electro optic switching was 67 μsec using a 50 V dc pulse and 8 V ac to latch the mixture.

EXAMPLE 9

The following liquid crystal mixtures contain compounds of formula I in which $-C.CN.R_2.R_3$ is a group of general formula:

[cyclohexyl with * , R$_4$, and CN substituents]

these compounds were prepared using the method outlined in route 1 shown in FIG. 1, starting from the appropriate cyclohexanone in step 1(ii).

A 1:1:1 by weight mixture of:

$C_8H_{17}$—[Ph]—[Ph]—COO—[Ph(F)]—$C_5H_{11}$ $C_8H_{17}O$—[Ph]—[Ph]—COO—[Ph(F)]—$C_5H_{11}$

-continued was used as the smectic host in each mixture.

(A)

this compound showed solid crystal (K) to isotropic liquid (I) transition at 122° C. Supercooling transitions $S_C^*$-$S_A$=107° C., $S_A$-I=108° C.

A 10 wt % mixture with the host showed:

S-$S_C$*45° C., $S_C$*-$S_A$ 72.5° C., $S_A$-N*129.5° C., N*-I 148° C.

| Temp (°C.) | Ps (nCcm$^{-2}$) |
| --- | --- |
| 50 | 6.3 |
| 55 | 5.2 |
| 60 | 5.0 |
| 65 | 4.0 |
| 70 | 2.3 |
| 75 | — |

(B)

compound mpt. 83° C.

A 10 wt % mixture with the host showed:

S-$S_C$*24° C., $S_C$*-$S_A$ 79.7° C.. $S_A$-N*110.4° C.N*-I 135° C.

| Temp (°C.) | Ps (nCcm$^{-2}$) |
| --- | --- |
| 30 | 24.9 |
| 40 | 21.3 |
| 50 | 18.2 |
| 55 | 16.0 |
| 60 | 14.7 |
| 65 | 12.4 |
| 70 | 10.0 |
| 75 | 6.9 |
| 80 | 0.7 |

(C)

this compound showed K-$S_A$ 146° C. ($S_C$*-$S_A$ 143° C.). $S_A$-I 147° C. A 10 wt % mixture with the host showed:

S-$S_C$*41° C., $S_C$*-$S_A$ 75.7° C., $S_A$-N*133° C., N*-I 151° C.

| Temp (°C.) | Ps (nCcm$^{-2}$) |
| --- | --- |
| 50 | 6.7 |
| 55 | 6.1 |
| 60 | 5.6 |
| 65 | 4.7 |
| 70 | 3.7 |
| 75 | 1.8 |

EXAMPLE 10

A ferroelectric smectic liquid crystal mixture was prepared which consisted of 10 wt % of the compound prepared in example 1 in solution in HI (see example 1). This had properties:

S-$S_C$*14° C., $S_C$*-$S_A$ 69° C., $S_A$-N*101.9° C. N*-I 134° C.

| temp (°C.) | Ps (nCcm$^{-2}$) |
| --- | --- |
| 40 | 17.8 |
| 45 | 15.6 |
| 50 | 13.8 |
| 55 | 11.3 |
| 60 | 8.7 |
| 65 | 5.1 |
| 70 | — |

An example of the use of a compound of Formula I in a liquid crystal material and device embodying the present invention will now be described with reference to FIG. 2.

Figure 2:
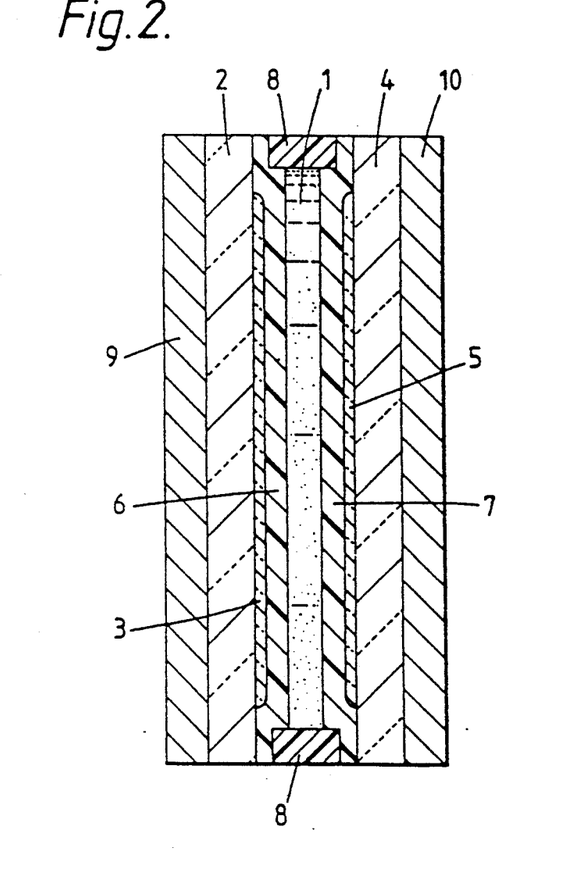
FIG. 2 Which shows a cross section through a liquid crystal electro-optic device.

In FIG. 2 a liquid crystal cell comprises a layer 1 of liquid crystal material exhibiting a chiral smectic phase sandwiched between a glass slide 2 having a transparent conducting layer 3 on its surface, e.g. of tin oxide or indium oxide, and a glass slide 4 having a transparent conducting layer 5 on its surface. The slides 2,4 bearing the layers 3,5 are respectively coated by films 6,7 of a polyimide polymer. Prior to construction of the cell the films 6 and 7 are rubbed with a soft tissue in a given direction the rubbing directions being arranged parallel upon construction of the cell. A spacer 8 e.g. of polymethyl methacrylate, separates the slides 2,4 to the required distance, e.g. 5 microns.

The liquid crystal material 1 is introduced between the slides 2,4 by filling the space between the slides 2,4 and spacer 8 and sealing the spacer 8 in a vacuum in a known way. Preferably the liquid crystal material is in the smectic A, nematic or isotropic liquid phase (obtained by heating the material) when it is introduced between the slides 2,4 to facilitate alignment of the liquid crystal molecules with the rubbing directions on the slides 2,4.

A polarizer 9 is arranged with its polarization axis parallel to the rubbing direction on the films 6,7 and an analyzer (crossed polarizer) 10 is arranged with its polarization axis perpendicular to that rubbing direction.

When a square wave voltage (from a conventional source not shown) varying between about +10 volts and −10 volts is applied across the cell by making contact with the layers 3 and 5 the cell is rapidly switched upon the change in sign of the voltage between a dark state and a light state as explained above.

In an alternative device (not shown) based on the cell construction shown in FIG. 2 the layers 3 and 5 may be selectively shaped in a known way, e.g. by photoetching or deposition through a mask, e.g. to provide one or more display symbols, e.g. letters, numerals, words or graphics and the like as conventionally seen on displays. The electrode portions formed thereby may be addressed in a variety of ways which include multiplexed operation.

The ferroelectric mixtures described in the preceding examples were suitable for use as the material 1.

We claim:

1. A compound suitable for use as a constituent of a ferroelectric smectic liquid crystal composition, being an ester of the formula:

where * indicates a chiral carbon atom and $R_4$ is $C_1$ to $C_6$ alkyl in a position on the cyclohexane such that the position indicated * is asymmetrically substituted, and X is a group of the formula:

where $R_1$ represents $C_1$ to $C_{12}$ alkyl or alkoxy, rings A, B and D each independently represent phenyl, chloro- or fluoro-substituted phenyl, or cyclohexyl; n is 0 or 1, Y may be $CH_2CH_2$ if n is 0, or may be a single bond, $CH_2CH_2COO$ or COO if n is 1.

2. A compound according to claim 1 characterized in that the cyclohexane ring is substituted by a single methyl group $R_4$.

3. A compound according to claim 2 characterized by a formula:

where $R_1$ represents $C_1$ to $C_{12}$ alkyl or alkoxy, rings A, B and D each independently represent phenyl, chloro- or fluoro-substituted phenyl, or cylcohexyl: n is 0 or 1, Y may be $CH_2CH_2$ if n is 0 or Y may be a single bond, $CH_2CH_2COO$ or COO if n is 1.

4. A compound according to claim 1 in which $R_1$ is $C_3$ to $C_{10}$ n-alkyl or n-alkoxy.

5. A compound according to claim 3 characterized by a formula:

6. A compound according to claim 3 characterized by a formula:

7. A compound according to claim 3 characterized by a formula

8. A ferroelectric smectic liquid crystal material being a mixture of at least two compounds, characterized in that at least one is a compound as claimed in claim 1.

9. A ferroelectric smectic liquid crystal material, being a mixture of at least two compounds characterized in that at least one is a compound as claimed in claim 3.

10. A liquid crystal electro-optic display device, characterized in that it uses a liquid crystal material as claimed in claim 8.

* * * * *